US010766829B2

(12) United States Patent
Nakagawa et al.

(10) Patent No.: US 10,766,829 B2
(45) Date of Patent: Sep. 8, 2020

(54) YEAST EXTRACT HAVING EFFECT OF PROMOTING GROWTH OF PLANT AND ELONGATION OF ROOT AND EFFECT OF IMPROVING ADDED VALUES OF PLANT

(71) Applicant: KOHJIN LIFE SCIENCES CO., LTD., Tokyo (JP)

(72) Inventors: Tomohiro Nakagawa, Oita (JP); Yoshie Yasumatsu, Oita (JP); Naoto Kaji, Oita (JP); Kenichi Ason, Oita (JP)

(73) Assignee: KOHJIN LIFE SCIENCES CO., LTD., Tokyo (JP)

( * ) Notice: Subject to any disclaimer, the term of this patent is extended or adjusted under 35 U.S.C. 154(b) by 142 days.

(21) Appl. No.: 15/558,791

(22) PCT Filed: Mar. 16, 2016

(86) PCT No.: PCT/JP2016/058325
§ 371 (c)(1),
(2) Date: Sep. 15, 2017

(87) PCT Pub. No.: WO2016/148193
PCT Pub. Date: Sep. 22, 2016

(65) Prior Publication Data
US 2018/0072634 A1  Mar. 15, 2018

(30) Foreign Application Priority Data
Mar. 19, 2015 (JP) ................. 2015-056668

(51) Int. Cl.
C05F 11/08 (2006.01)
C05G 5/23 (2020.01)
(Continued)

(52) U.S. Cl.
CPC ............... C05F 11/08 (2013.01); A01G 7/06 (2013.01); A01G 24/00 (2018.02); A01N 63/10 (2020.01);
(Continued)

(58) Field of Classification Search
None
See application file for complete search history.

(56) References Cited

U.S. PATENT DOCUMENTS 6,416,982 B1 * 7/2002 Zhang ................... C05F 11/08
424/93.21
9,403,732 B2 * 8/2016 LeSueur ................ C05F 17/00
(Continued)

FOREIGN PATENT DOCUMENTS

JP 63-45211 2/1988
JP 04-077381 3/1992
(Continued)

OTHER PUBLICATIONS

Naomi Obara et al., "Mechanism of PR gene expression by treatment of tobacco leaves with yeast extract", Japanese Journal of Phytopathology, 73 (2); 2007; pp. 94-101, with English translation.
(Continued)

Primary Examiner — Wayne A Langel
(74) Attorney, Agent, or Firm — Greenblum & Bernstein, P.L.C.

(57) ABSTRACT

[Problem] The present invention seeks to provide a composition for plants that is highly safe and that contributes to early harvesting, increasing yield, and increasing added value of crops. Specifically, the present invention provides a yeast extract that, by addition to a foliar surface spray or to soil or water, provides an effect of promoting growth, an effect of root lengthening, an effect of improved taste, and an effect of increased amino acid content of a plant. A substance
(Continued)

obtained from yeast that is edible and considered to be safe is preferred as the yeast extract.

[Means for Solving the Problem] A yeast extract having a peptide content of 5 wt % or more and an RNA content of 5 wt % or more is sprayed onto or provided as fertilizer to a plant. The yeast extract is preferably derived from *Candida utilis*, which is edible and considered to be safe.

17 Claims, 7 Drawing Sheets

(51) Int. Cl.
| | |
|---|---|
| *A01G 7/06* | (2006.01) |
| *A01G 24/00* | (2018.01) |
| *C05G 1/00* | (2006.01) |
| *C05F 9/02* | (2006.01) |
| *C05F 9/00* | (2006.01) |
| *A01N 63/10* | (2020.01) |
| *A01N 63/30* | (2020.01) |
| *C12N 1/16* | (2006.01) |

(52) U.S. Cl.
CPC ............... *A01N 63/30* (2020.01); *C05F 9/00* (2013.01); *C05F 9/02* (2013.01); *C05G 1/00* (2013.01); *C05G 5/23* (2020.02); *C12N 1/16* (2013.01); *Y02A 40/214* (2018.01); *Y02A 40/215* (2018.01)

(56) References Cited

U.S. PATENT DOCUMENTS

| | | | |
|---|---|---|---|
| 10,053,393 B2* | 8/2018 | LeSueur | C05F 17/00 |
| 2014/0113814 A1* | 4/2014 | Chambers | C05G 3/60 |
| | | | 504/100 |
| 2014/0234526 A1 | 8/2014 | Yasumatsu et al. | |
| 2016/0186273 A1* | 6/2016 | Taghavi | A01N 63/00 |
| | | | 504/100 |
| 2018/0002243 A1* | 1/2018 | Temme | C05C 1/00 |
| 2018/0072633 A1* | 3/2018 | Dent | A01N 63/00 |

FOREIGN PATENT DOCUMENTS

| | | | |
|---|---|---|---|
| JP | 04-134007 | | 5/1992 |
| JP | 2002-305998 | | 10/2002 |
| JP | 2004-196679 | | 7/2004 |
| JP | 2006-265199 | | 10/2006 |
| JP | 2007-131562 | | 5/2007 |
| JP | 2009-269852 | | 11/2009 |
| JP | 2013-21989 | | 2/2013 |
| JP | 5763282 | | 8/2015 |
| WO | 2006/059683 | | 6/2006 |
| WO | 2013/031571 | * | 3/2013 |

OTHER PUBLICATIONS

Yoshiki Aoyagi et al., "Development of high functional Yeast Extract and application of it to foods", Food Preservation Science, 27 (2); 2001; pp. 99-106, with English translation.
International Search Report issued in Patent Application No. PCT/JP2016/058325, dated Jun. 14, 2016.

* cited by examiner

[FIG. 1]
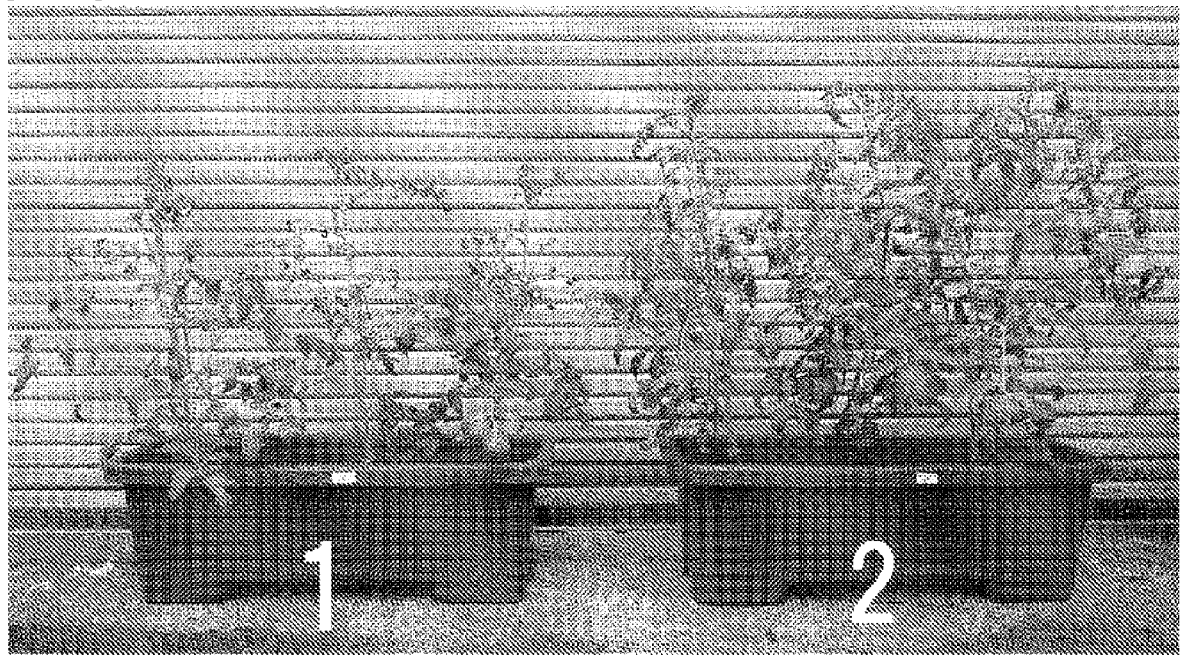
[FIG. 2]
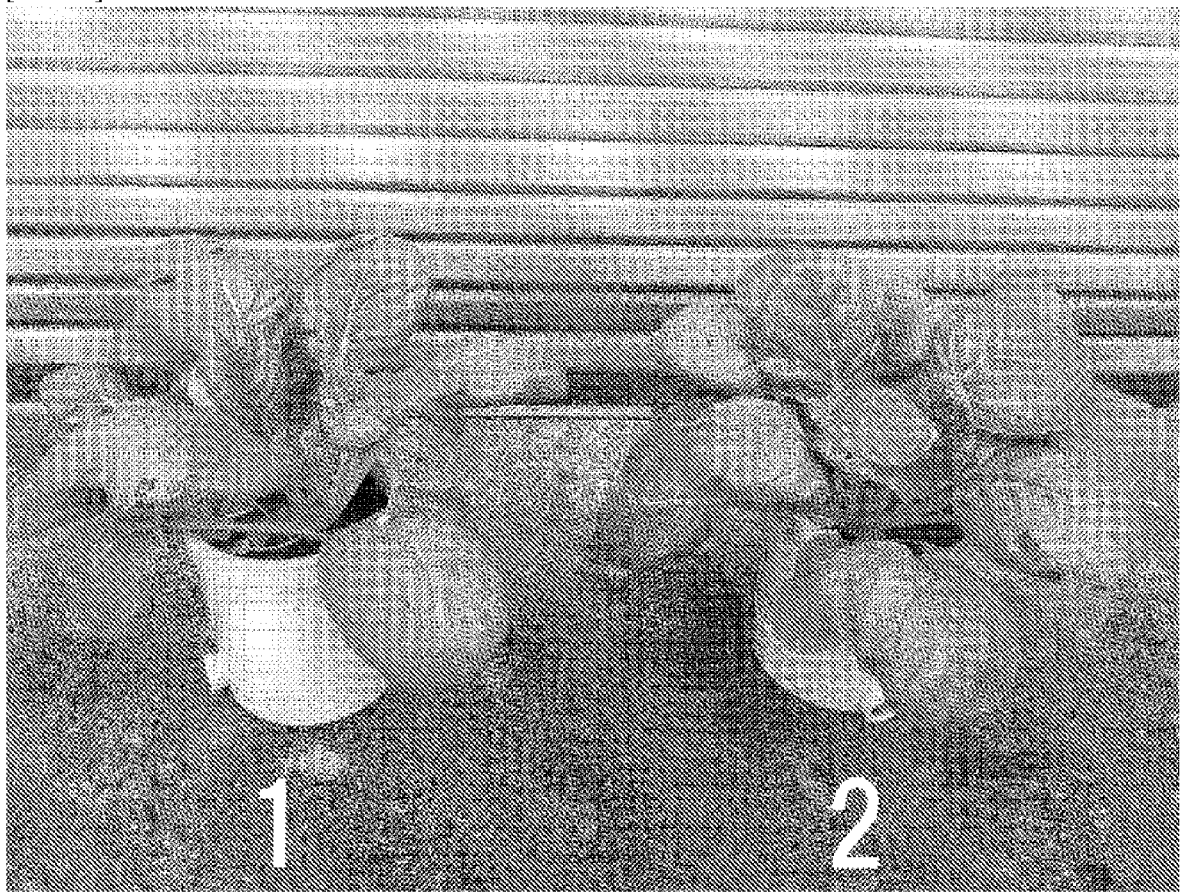

[FIG. 3]
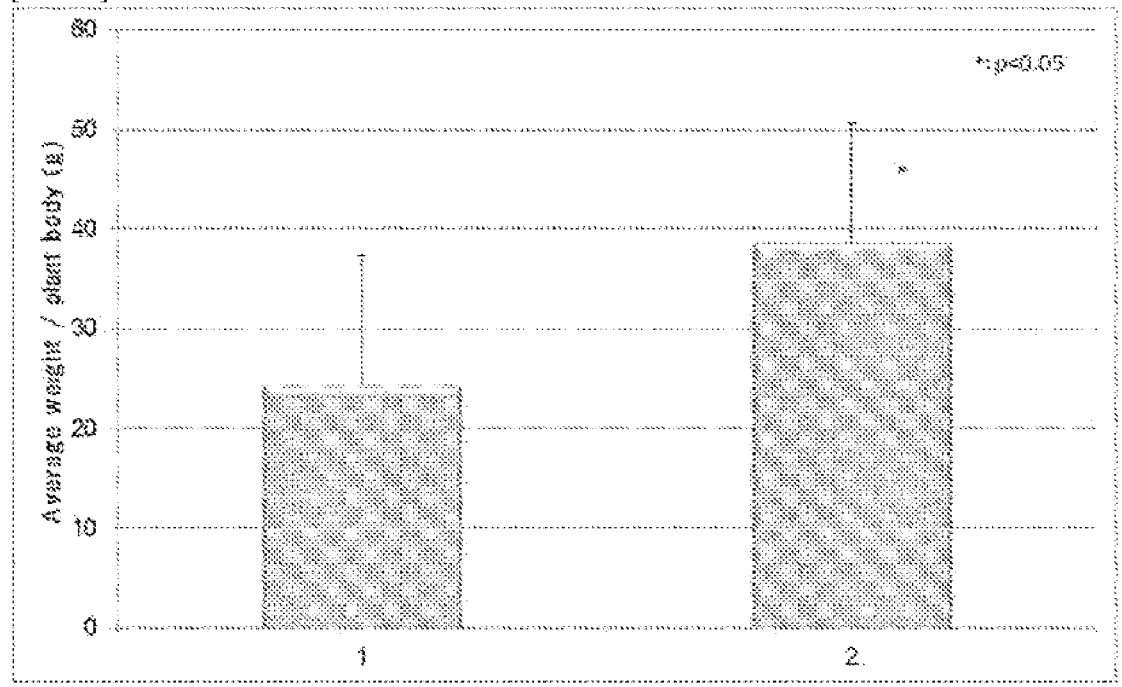
[FIG. 4]
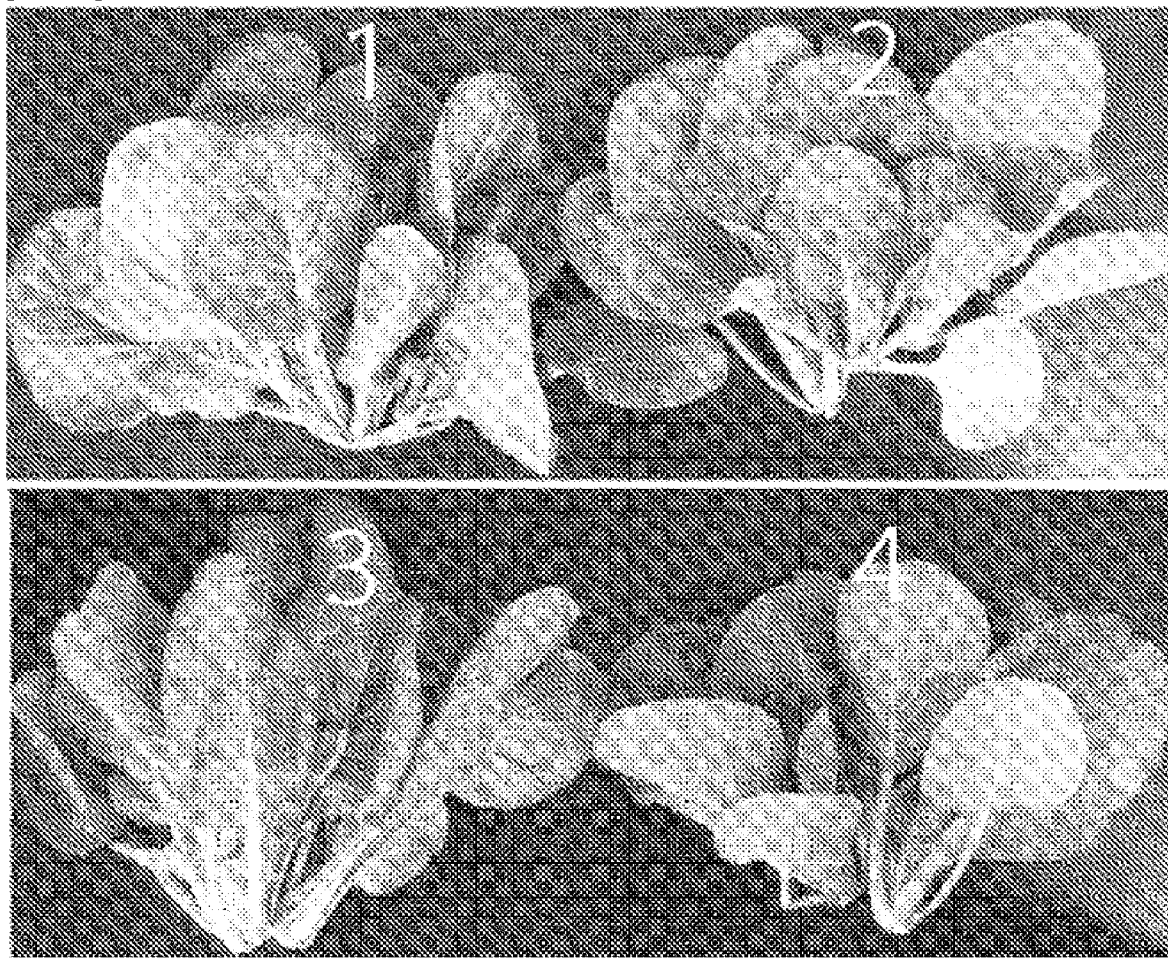

[FIG. 5]
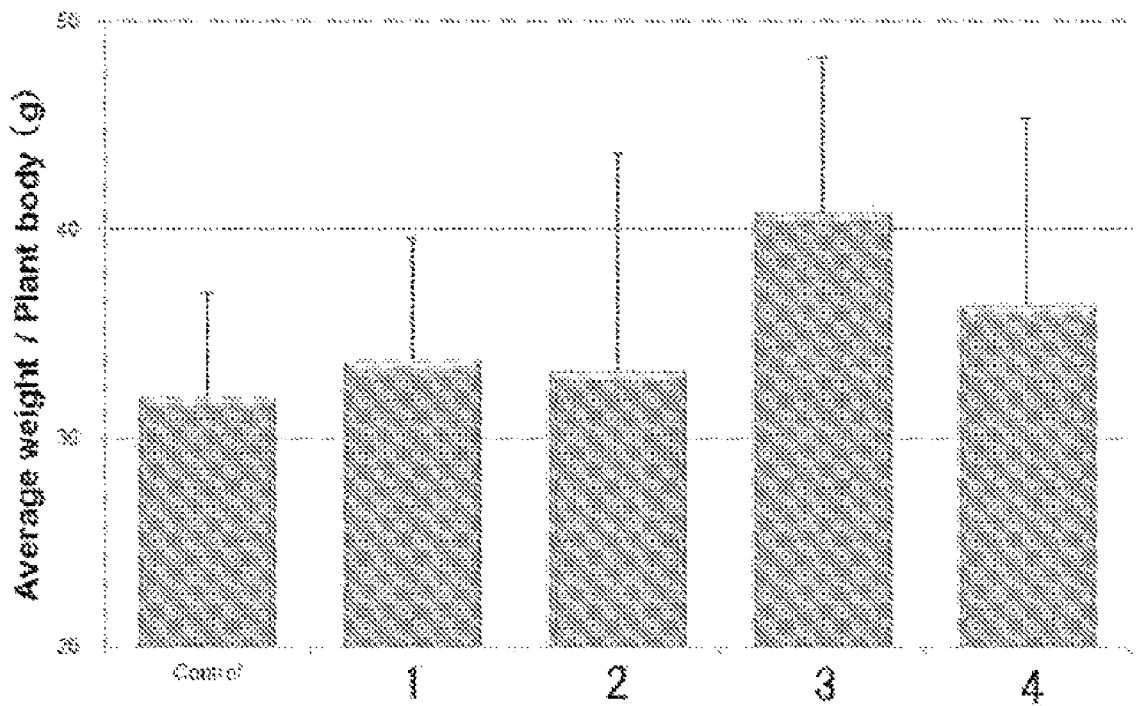
[FIG. 6]
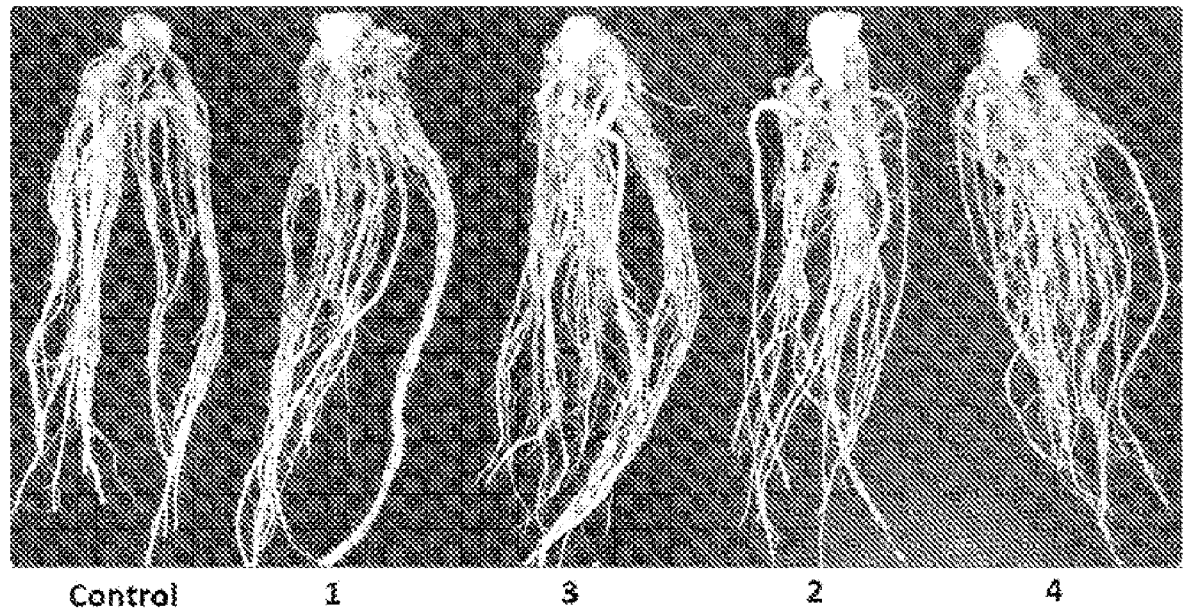

[FIG. 7]
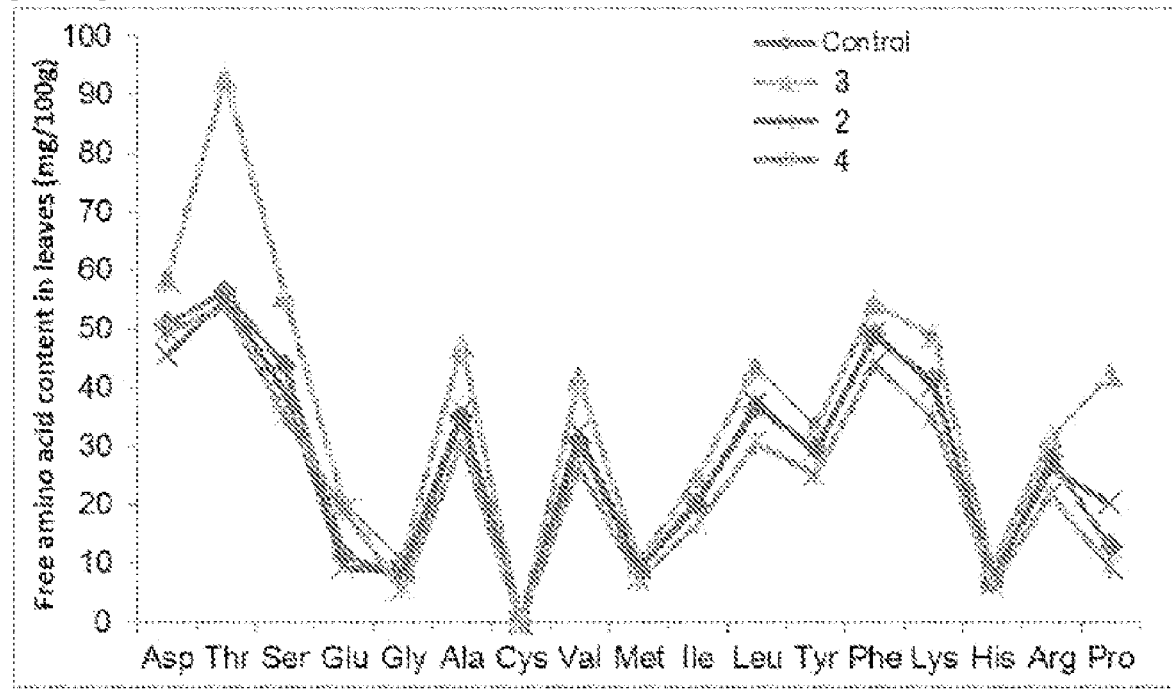
[FIG. 8]
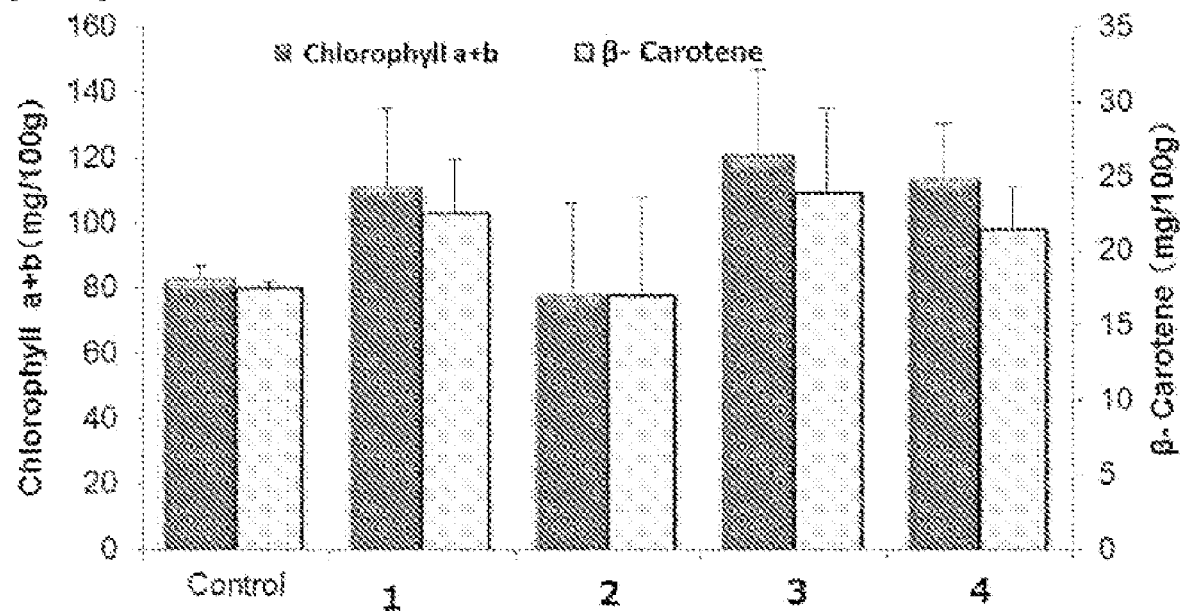

[FIG. 9]
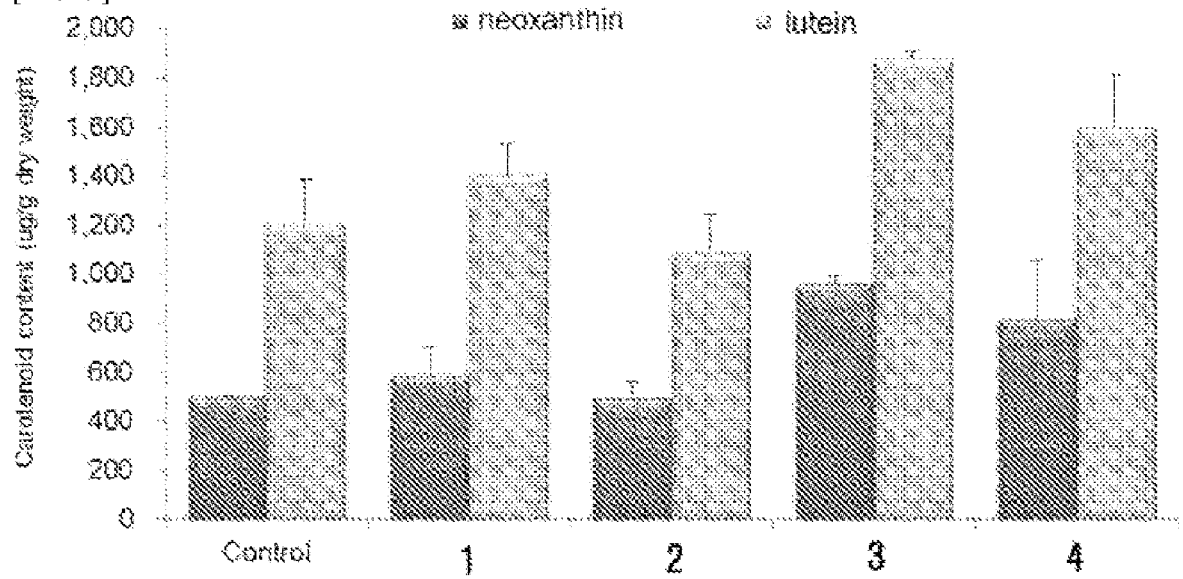
[FIG. 10]
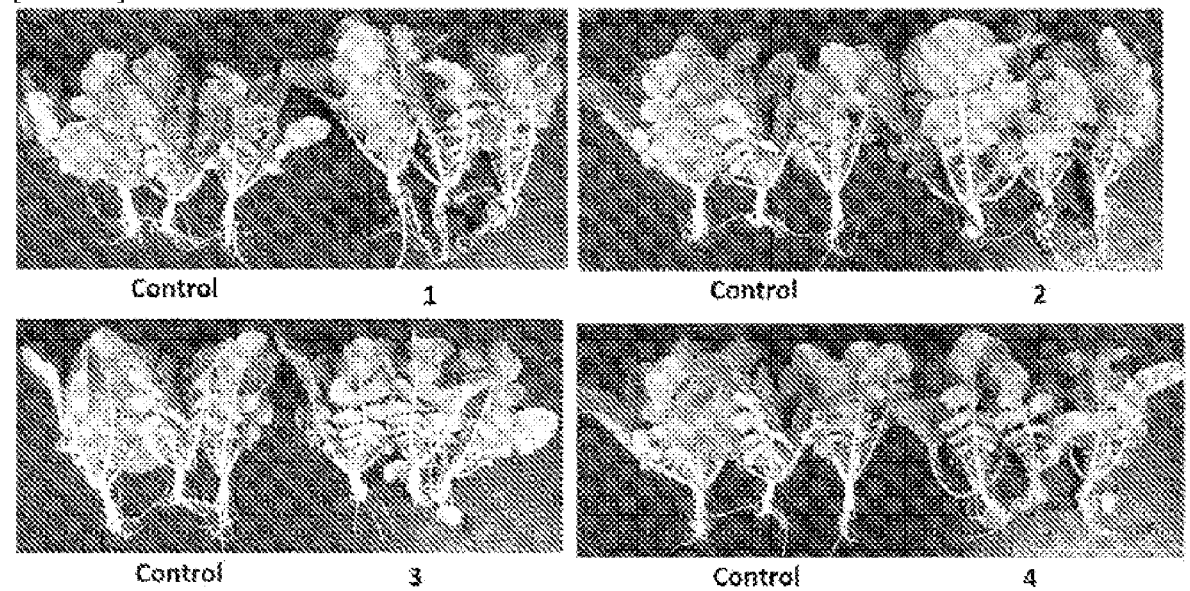

[FIG. 11]
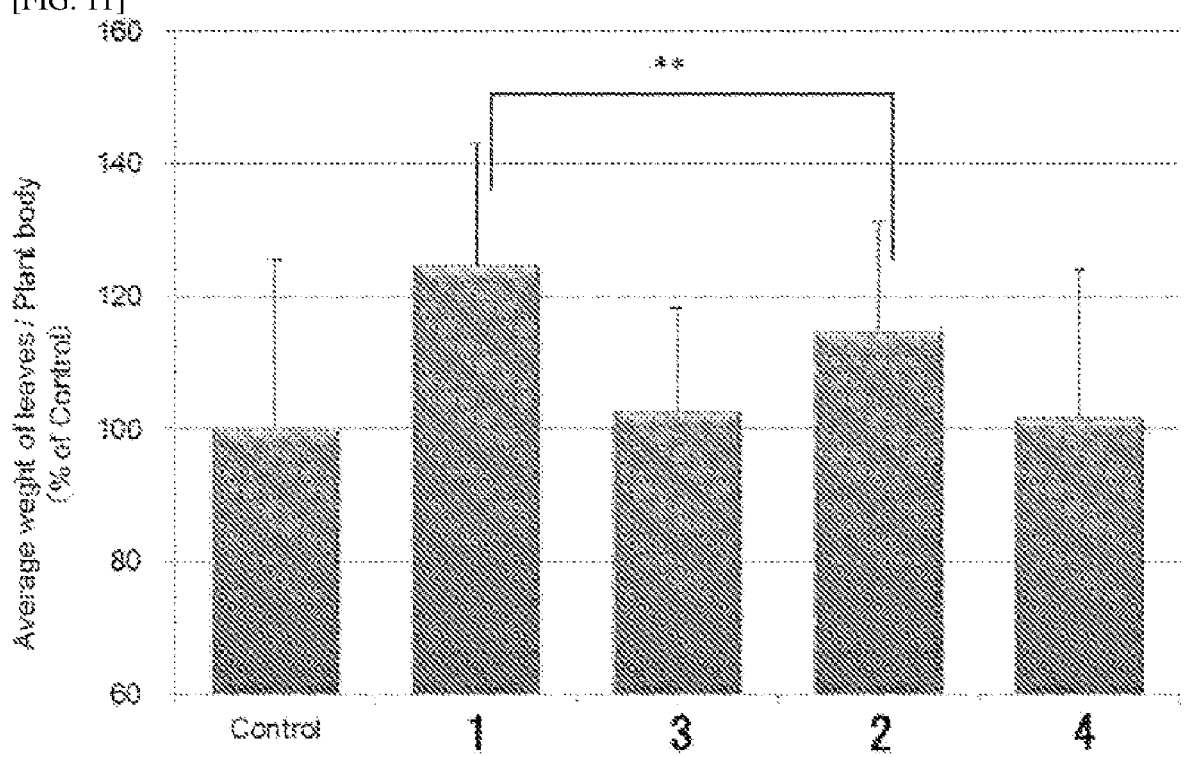
[FIG. 12]
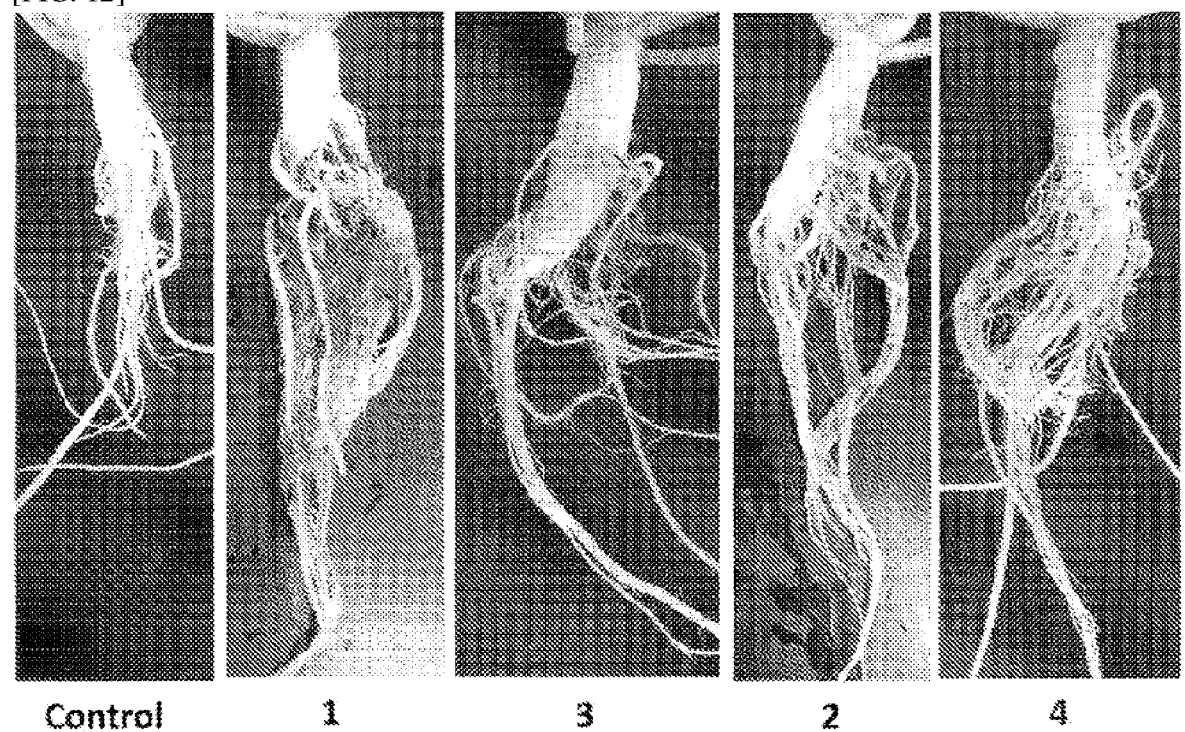

[FIG. 13]
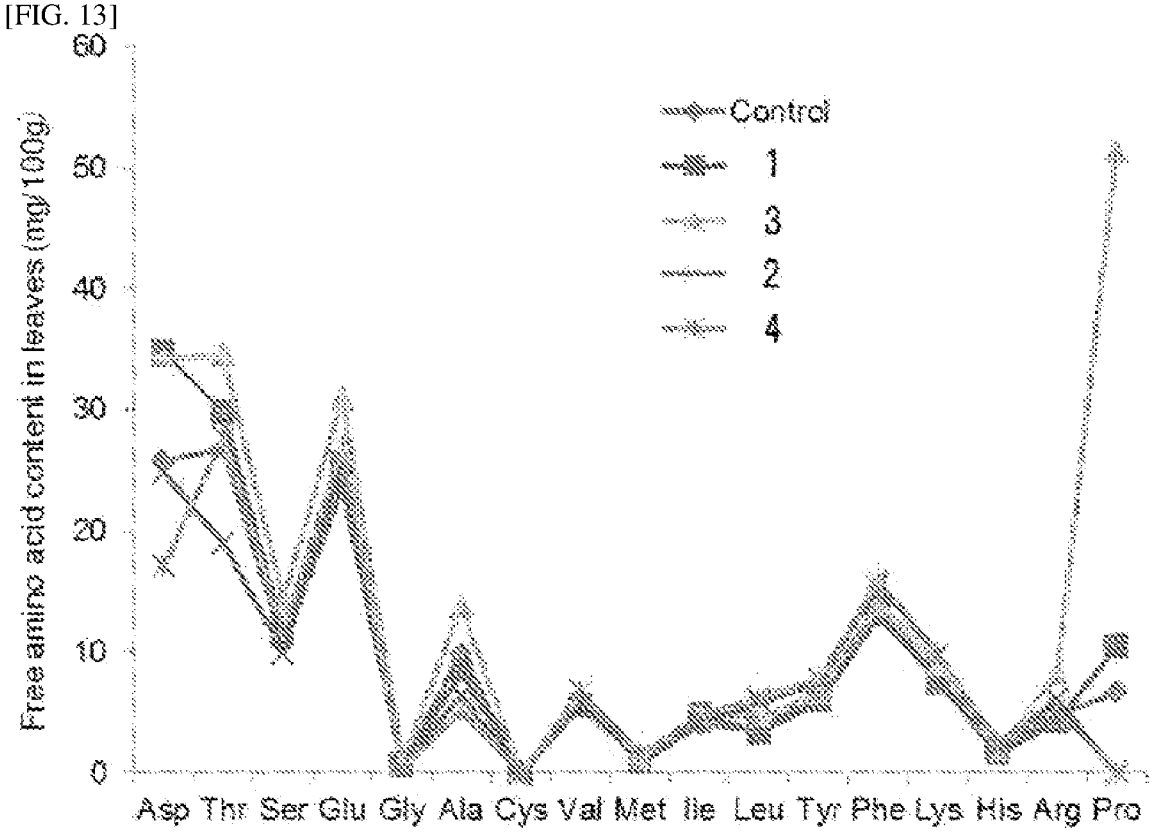

YEAST EXTRACT HAVING EFFECT OF PROMOTING GROWTH OF PLANT AND ELONGATION OF ROOT AND EFFECT OF IMPROVING ADDED VALUES OF PLANT

FIELD OF THE INVENTION

The present invention relates to a yeast extract having an effect of promoting growth of a plant, an effect of root lengthening, an effect of improving taste, and an effect of increasing content of nutritive components and the like.

BACKGROUND OF THE INVENTION

In order to increase yield and improve quality of crops such as fruits and vegetables, various growth promoting agents, plant growth adjustment agents, physiological activity promoting agents, taste improvement agents, and the like that are sprayed onto leaf surfaces of fruits and vegetables or onto soil have been suggested. In recent years, focus has also fallen on vegetables having standardized functional ingredients such as lycopene and potassium.

Known examples include a foliar surface spray for grapes that contains calcium formate and a boron compound (Patent Literature 1), and a growth promoting agent and physiological activity promoting agent that are sprayed on soil or a leaf surface and have a nucleic acid-based component such as nucleotides as an active ingredient (Patent Literatures 2 and 3). For supplying a nitrogen component via a leaf surface, Patent Literature 4 describes using not only urea nitrogen but also an amino acid nitrogen, and employing a substance in which protein from albumen or powdered fat-free milk has been fermented with yeast. In addition, a cell wall decomposition product derived from brewer's yeast is known to improve the taste of an edible portion of a plant (Patent Literature 5). A composition for plants has been sought that broadly brings together these effects of promoting growth and improving quality of crops, has an elevated effect, and that is safer and easy to handle.

RELATED ART

Patent Literature

Patent Literature 1: Japanese Patent Laid-open Publication No. H4-134007
Patent Literature 2: Japanese Patent Laid-open Publication No. 2004-196679
Patent Literature 3: Japanese Patent Laid-open Publication No. H4-77381
Patent Literature 4: Japanese Patent Laid-open Publication No. 2006-265199
Patent Literature 5: Japanese Patent Laid-open Publication No. 2007-131562

SUMMARY OF THE INVENTION

Problem to Be Solved by the Invention

The present invention seeks to provide a composition for plants that is highly safe and that contributes to early harvesting, increasing yield, and increasing added value of crops. Specifically, the present invention provides a yeast extract that, by addition to a foliar surface spray or to soil or water, provides an effect of promoting growth, an effect of root lengthening, an effect of improved taste, and an effect of increased amino acid content of a plant. In addition, from a safety standpoint, a substance obtained from yeast that is edible and considered to be safe is preferred.

Means for Solving the Problem

The inventors of the present invention have discovered that a yeast extract obtained from Torula yeast (*Candida utilis*), which is edible and considered to be safe, the yeast extract containing RNA and peptide, has an effect of promoting plant growth and an effect of root lengthening that are greater than the effects of an RNA isolate. Moreover, the inventors discovered that the yeast extract has an effect of increasing various added values, such as increasing amino acid content and improving taste. The yeast extract according to the present invention can be used in order to promote growth and promote root lengthening for all plants, including vegetables, and furthermore can be used to increase added values such as improving taste and increasing amino acid content.

Specifically, the present invention relates to:
(1) A composition for plants containing a yeast extract having a peptide content of 5 wt % or more and an RNA content of 5 wt % or more;
(2) The composition for plants according to (1), in which the yeast extract has a peptide content of 15 wt % or more, an RNA content of 25 wt % or more, and a free amino acid content of 4 wt % or less;
(3) The composition for plants according to (1) or (2), in which the yeast extract is extracted from *Candida utilis* bacterial cells;
(4) A method of cultivating a plant in which the composition for plants according to any one of (1) to (3) is sprayed onto a leaf surface of a plant, or is added to soil or a hydroponic solution used in plant cultivation.

Effect of the Invention

By adding the yeast extract according to the present invention to a foliar surface spray, soil, or the like of a plant, not only does the yeast extract provide excellent effects of promoting growth and promoting root lengthening, but the yeast extract also exhibits an effect of increasing added value, for example increasing content of a nutritive component such as amino acids or improving taste, in a fruiting vegetable such as a tomato, a leaf vegetable such as Japanese mustard spinach or Japanese radish leaf, or root vegetables or fruits. In addition, by using Torula yeast, which is edible and considered to be safe, as the source for the yeast extract, the present invention is safe to handle and the resulting crops are also safe for use as foodstuffs.

BRIEF DESCRIPTION OF THE DRAWINGS

FIG. 1 An effect of promoting growth of a tomato.
FIG. 2 An effect of promoting growth of Japanese mustard spinach.
FIG. 3 An effect of increasing yield of Japanese mustard spinach.
FIG. 4 A comparison test with RNA of the effect of promoting growth of Japanese mustard spinach.
FIG. 5 A comparison test with RNA of the effect of increasing yield of Japanese mustard spinach.
FIG. 6 A comparison of a root portion of Japanese mustard spinach.
FIG. 7 An effect on free amino acid content of Japanese mustard spinach.

FIG. 8 An effect on chlorophyll and β-carotene content of Japanese mustard spinach.

FIG. 9 An effect on neoxanthin and lutein content of Japanese mustard spinach.

FIG. 10 A comparison test with RNA of the effect of promoting growth of Japanese radish leaf.

FIG. 11 A comparison test with RNA of the effect of increasing yield of Japanese radish leaf.

FIG. 12 A comparison of the root portion of Japanese radish leaf.

FIG. 13 An effect on free amino acid content of Japanese radish leaf.

MODE FOR CARRYING OUT THE INVENTION

A detailed description of the present invention is given below. Examples of the yeast used in producing the yeast extract used in the present invention are not particularly limited and may include baker's yeast, brewer's yeast (*Saccharomyces cerevisiae*), and Torula yeast (*Candida utilis*). Among these yeasts, use of Torula yeast is preferred, the Torula yeast generally containing a high amount of RNA.

The yeast extract used in the present invention is extracted from yeast cell bodies preferably containing 6.5 wt % or more of RNA, and more preferably containing 10 wt % or more of RNA. Methods of increasing RNA content in the yeast cell bodies are publicly known and are, for example, recited in Japanese Examined Patent Publication No. S54-46824, Japanese Patent Laid-open Publication No. H11-196859, and Japanese Patent Laid-open Publication No. 2009-207464. Japanese Examined Patent Publication No. S54-46824 provides a specific description. After using ultraviolet rays, X-rays, a mutation agent, or the like on a yeast, cells having unchanged growth at normal temperature in a synthetic medium and a notably slower growth speed than the parent cell at low temperature are selected. When these cells are cultivated at low temperature in a culture medium with an added antibiotic substance selectively affecting only growth cells of yeast, mutant cells which are sensitive to low temperatures are concentrated. Each cell having greater sensitivity to low temperatures are selected from among these cells, then this mutant cell having high RNA content and having favorable yield with almost no change in growth speed at normal temperature is further screened from among these to obtain a target mutant cell.

Such yeast cell bodies are cultivated, harvested, and washed to obtain cell bodies. Next, enzymes within the yeast cell bodies are deactivated by hot water such that autolysis does not occur in the cell bodies. After a cell wall lytic enzyme acts on the cell bodies, solid content is separated out and the resulting extract is concentrated, sterilized, and dried, thereby achieving manufacture of the yeast extract of the present invention. In the above process, when a nucleolytic enzyme or a protease act on the extract, RNA content and peptide content are unlikely to reach a specified amount, and therefore this is not preferred. In a case where the RNA content and peptide content in the yeast extract do not reach the specified amount, concentration may be performed with a known method.

The peptide of the present invention refers to two or more amino acids having a peptide bond. The peptide content is calculated by subtracting the free amino acid content from the total amino acid content.

The yeast extract according to the present invention contains 5 wt % or more of a peptide, preferably 10 wt % or more of the peptide, and more preferably 15 wt % or more of the peptide; and contains 5 wt % or more of RNA, preferably 10 wt % or more of RNA, and more preferably 25 wt % or more of RNA. The peptide content is preferably high, and in order to achieve this, the free amino acid content is kept low, preferably to 4 wt % or less.

The yeast extract is a food and has substantially no particular adverse effect on the environment or human body, and is therefore suited to organic farming of plants. The yeast extract can also be applied to agriculture that uses no synthetic chemical substances.

The yeast extract of the present invention may be used without modification, or may be combined with another component to create a composition for plants, and can be used in the cultivation and growth of plants. The type of plant and purpose for which the composition for cultivation of plants according to the present invention is used are not particularly limited. The composition can, for example, be used in order to promote growth, promote root lengthening, improve quality of taste, or increase amino acid content of a vegetable (tomato, Japanese mustard spinach, Japanese radish leaf, spinach, onion, and the like) or a fruit (grapes, apple, pear, melon, strawberries, and the like). By promoting lengthening of roots, a nutrient absorption rate is also improved, and growth of the vegetable or fruit is promoted. As a result, an increased yield or early harvesting become possible. In addition, the quality of taste and nutritional value of the harvested product also increase, and added value also increases.

A form of the composition for plants according to the present invention is not particularly limited, and may take the form of a tablet, granules, a powder, or a liquid, for example. During distribution and storage, the composition may take the form of a tablet, granules, powder, or a concentrated liquid, and by adding water and dissolving the composition at the time of use, the composition can be used at an appropriate concentration. When used as a foliar surface spray or soil spray, the concentration at the time of use of the composition for plants according to the present invention is, in terms of dry weight of the yeast extract, preferably between 1.0 and 100,000 ppm, and more preferably between 10 and 1,000 ppm. By having the concentration of the yeast extract in a foliar surface spray liquid or the like within this range, the yield and nutritional value of a crop are improved.

A more optimal concentration when performing foliar surface spray differs according to the type of plant and purpose. For example, when the purpose is promoting growth of Japanese mustard spinach, or when the purpose is increasing the amino acid content, neoxanthin content, or lutein content, the concentration of the yeast extract according to the present invention is preferably 200 mg/L or more. Meanwhile, when the purpose is increasing the chlorophyll content or β-carotene content in leaves of Japanese mustard spinach, a concentration of 100 mg/L is sufficient. When the purpose is promoting growth of Japanese radish leaf, the concentration of the yeast extract according to the present invention is preferably 200 mg/L or less. Meanwhile, when the purpose is increasing the free amino acids in the leaves of Japanese mustard spinach, and particularly increasing the threonine content or proline content, the concentration is preferably 200 mg/L or more. During actual use of the yeast extract according to the present invention, a concentration believed to be optimal may be determined according to the purpose or in consideration of a balance between a plurality of purposes.

Frequency of spraying the composition for plants according to the present invention is not particularly limited, and is preferably performed once every one to 100 days, and more preferably once every seven to ten days. Moreover, the composition for plants may be used independently, or may be used in combination with fertilizer or gardening culture soil. Examples of the fertilizer may include a chemical fertilizer containing nitrogen, phosphorous, or potassium, or an organic fertilizer such as plant oil cakes, fish meal, or powdered marine algae. A method of applying the composition for plants may be a generic method. Examples may include spraying or spreading on the leaf surface of the plant, adding to the soil or hydroponic culture solution, or the like.

In the present invention, a method of measuring each component is as noted below.

(Method of Measuring RNA)

RNA content in a sample was measured using high performance liquid chromatography (HPLC).

HPLC Conditions

Separation column: Asahipak HPLC column GS-320 (30° C., 7.5 mm×300 mm, manufactured by Showa Denko)

Mobile phase: 0.1 M sodium phosphate buffer solution (pH 7.0)

Flow speed: 1.0 mL/min

Detection: Ultraviolet detector (260 nm)

(Method of Measuring Peptide)

For peptide content in a sample, total amino acid and free amino acid were measured using an amino acid analyzer (Hitachi high-speed amino acid analyzer L-8900), and the total amino acid minus the free amino acid was taken as the peptide content.

(Method of Measuring Free Amino Acid)

Free amino acid content in a sample was measured using the amino acid analyzer (Hitachi high-speed amino acid analyzer L-8900).

(Method of Measuring Dietary Fiber)

For an amount of dietary fiber in a sample, an enzymatic-gravimetric method was used which utilizes protease or amyloglucosidase.

(Method of Measuring Chlorophyll and (β-carotene)

A sample leaf (1 g) was homogenized in 20 mL acetone-hexane (volume ratio 4:6) solution, after which light absorbency of a supernatant (663 nm, 645 nm, 505 nm, 453 nm) was measured and, using the formulas below, a concentration of each component was calculated.

Chlorophyll a concentration (mg/100 mL)=$0.999A_{665}-0.0989A_{645}$

Chlorophyll b concentration (mg/100 mL)=$-0.328A_{665}+1.77A_{645}$

β-carotene concentration (mg/100 mL)=$0.216A_{665}-1.22A_{645}-0.304A_{505}+0.452A_{453}$ (Where $A_{663}$, $A_{645}$, $A_{505}$, and $A_{453}$ are light absorbency at 663 nm, 645 nm, 505 nm, and 453 nm, respectively.)

(Method of Measuring Neoxanthin and Lutein)

A freeze-dried product of a sample was extracted overnight in acetone, after which the solid content was removed and the resulting extraction liquid was dried in an evaporator. This was dissolved in a methanol:acetonitrile=7:3 solvent and was passed through a filtration filter, after which the neoxanthin and lutein were measured by HPLC.

HPLC Conditions

Model name: HITACHI LaChrom

Column: TSK gel ODS-80™

Mobile phase: Acetonitril:water (9:1) (A), ethyl acetate (B)

Flow speed: 1.5 mL/min

Detection absorbency: 450 nm

Gradient conditions: 0 to 20 minutes A:B=100:0 50:50, 20 to 30 minutes A:B=50:50, 30 to 35 minutes A:B=50:50→100:0

EMBODIMENTS

The present invention is described in detail in embodiments below. The present invention, however, is not limited to the embodiments.

<Exemplary Manufacture 1> Acquiring Yeast Extract

Using a 10 N sulfuric acid, 1000 ml of a 10% cell body suspension of *Candida utilis* CS 7529 strain (FERM BP-1656) was adjusted to a pH of 3.5, then was subjected to a heat treatment at 60° C. for 30 minutes, after which the cell bodies were collected via centrifugal separation and cleaned with water to remove the sulfuric acid and superfluous extracts. After the cell bodies were adjusted to a cell body concentration of 10% and suspended using water, a heat treatment was performed at 90° C. for 30 minutes; enzymes within the cell bodies were completely deactivated; the suspension was adjusted to 40° C. and a pH of 7.0; 0.5 g of a cell wall lytic enzyme ("Tunicase," manufactured by Daiwa Kasei) was added thereto to react for four hours; and the extract was extracted. Cell body residue was removed by centrifugal separation, then a supernatant fluid thus obtained was condensed and spray-dried to obtain 30 g of yeast extract powder. The obtained yeast extract contained 18.7 wt % of peptide, 30.4 wt % of RNA, 0.5 wt % of free amino acid, and 22.7 wt % of dietary fiber.

<Embodiment 1> Growth Promoting Effect on Tomato

Using commercially available "flower and vegetable soil" as the soil, tomato (Momotaro) seeds were sown in pots and, after fifteen days from sowing, the tomatoes were permanently planted with three stalks per planter (80×30 cm) using "flower and vegetable soil" as the soil. The yeast extract obtained by Exemplary Manufacture 1 was dissolved in water to a concentration of 300 mg/L to produce a foliar surface spray liquid, and after one week of permanent planting, foliar surface spraying was performed every ten days. Spraying was performed until an underside of the leaves was completely wet. After two months, a growth status of the plants was checked. No particular temperature control was performed. As a control, a tomato plant was also made that was sprayed with water instead of the aqueous solution of yeast extract.

Results of Embodiment 1 are shown in FIG. 1. The control is "1," and the test field that was subjected to foliar surface spraying with the yeast extract solution of the present invention is "2." As shown in FIG. 1, the plants subjected to foliar surface spraying with the 300 mg/L aqueous solution of yeast extract exhibited a clear effect of promoted growth as compared to the control.

<Embodiment 2> Growth Promoting Effect on Japanese Mustard Spinach

Japanese mustard spinach (*Brassica rapa* var. *perviridis*) is a plant of the family Brassicaceae, and is a vegetable with high nutritional value. Primarily the leaves and stem portions of Japanese mustard spinach are consumed. Using commercially available "flower and vegetable soil" as the soil, Japanese mustard spinach seeds were sown in pots (16 cm×16 cm×17 cm). After true leaves appeared, foliar surface spraying was performed every ten days using the 300 mg/L aqueous solution of the yeast extract obtained by Exemplary Manufacture 1, and after 90 days from planting the seeds, the Japanese mustard spinach was harvested. Foliar surface spray was misted onto the plants until the underside of the leaves was completely wet. No particular temperature control was performed. As a control, a Japanese mustard spinach plant was also made that was sprayed with water instead of the aqueous solution of yeast extract. The control was handled similarly in Embodiments 3 onward.

Results of Embodiment 2 are shown in FIGS. 2 and 3. The control is "1," and the test field that was subjected to foliar surface spraying with the yeast extract solution of the present invention is "2." As shown in FIG. 2, the plants subjected to foliar surface spraying with the 300 mg/L aqueous solution of yeast extract exhibited a clear effect of promoted growth as compared to the control. Also, as shown in FIG. 3, a weight of each stalk of Embodiment 2 significantly increased relative to the control. In this way, by spraying the yeast extract according to the present invention onto the plants, the yeast extract exhibits a clear effect of promoting plant growth, and an increased yield and early harvest of crops can be expected.

In general, RNA is said to have an effect of promoting growth, and the effect of promoting growth exhibited by Embodiments 1 and 2 may be construed as also arising solely from the RNA in the yeast extract. In view of the above, in order to test whether the effect of promoting growth exhibited by the yeast extract according to the present invention is an effect due solely to the RNA in the yeast extract, a comparative test was conducted of the yeast extract according to the present invention and an equivalent amount of RNA isolate.

<Embodiment 3> Comparison of Effects of Yeast Extract and RNA on Japanese Mustard Spinach Using commercially available "flower and vegetable soil" as the soil, Japanese mustard spinach seeds were sown in planters (80 cm×30 cm). After sprouting, the Japanese mustard spinach was permanently planted in a field and, after the true leaves appeared, the foliar surface spray liquid was misted onto the plants until the underside of the leaves was wet, at an interval of once in ten days. No temperature control was performed during cultivation, and the plants were harvested 90 days after permanent planting. The foliar surface spray liquid was as follows.
1: 100 mg/L aqueous solution of yeast extract obtained by Exemplary Manufacture 1.
2: 30 mg/L aqueous solution of RNA (manufactured by OMTEK). This is equivalent to the RNA concentration of the 100 mg/L aqueous solution of yeast extract in 1 above.
3: 300 mg/L aqueous solution of yeast extract obtained by Exemplary Manufacture 1.
4: 90 mg/L aqueous solution of RNA (manufactured by OMTEK). This is equivalent to the RNA concentration of the 300 mg/L aqueous solution of yeast extract in 3 above.
5: Water (control)

Evaluation was performed of an apparent size of a harvested edible portion and roots, an average weight of the edible portion, amino acid content, chlorophyll a+b content, β-carotene content, neoxanthin content, lutein content, and taste. For the taste evaluation, an experienced panel of six individuals was fed the edible portion without knowing which was the test field, and comments were obtained on differences in taste.

Results of Embodiment 3 are shown in FIGS. 4 to 8. FIG. 4 is a photograph of the edible portion of the harvested Japanese mustard spinach. Numbers 1 to 4 indicate the respective type of foliar surface sprays noted above. FIG. 5 indicates the weight of the edible portion of the harvested Japanese mustard spinach. Numbers 1 to 4 indicate the respective type of foliar surface sprays noted above.

In FIGS. 4 and 5, when comparing numbers 3 and 4, there is a marked difference in size and yield, and the yeast extract according to the present invention clearly exhibits an elevated effect of promoting growth as compared to an equivalent amount of RNA isolate. This result indicates that the peptides or the like, which are components other than RNA in the yeast extract, also contribute to promoting growth.

Moreover, when comparing numbers 1 and 3 (that is, the 100 mg/L aqueous solution of yeast extract and the 300 mg/L aqueous solution of yeast extract), number 3 was significantly larger and also had an increased yield relative to the control. Therefore, this indicates that when the purpose is to increase yield, the concentration of the yeast extract according to the present invention in the foliar surface spray liquid is preferably 300 mg/L rather than 100 mg/L.

FIG. 6 is a photograph of root portions of the harvested Japanese mustard spinach, and numbers 1 to 4 indicate the respective type of foliar surface sprays noted above. In addition to the effect of promoting growth of the edible portion, an effect of promoting root lengthening was also observed in the root portions (lateral roots and root hairs). The effect was higher for numbers 1 and 3, which were sprayed with the aqueous solutions of yeast extract according to the present invention, than for numbers 2 and 4, which are RNA isolates.

FIG. 7 indicates results of measuring the free amino acid content in a leaf of the harvested Japanese mustard spinach. Plants that were sprayed with RNA had a free amino acid content that was even lower than the control. In comparison, plants that were sprayed with the 300 mg/L aqueous solution of yeast extract according to the present invention generally had a higher amino acid content, of which threonine (Thr) and proline (Pro) were characteristic, and values for each were two to three times higher than for the control. Given this, a component other than RNA in the yeast extract is believed to contribute to improving amino acid content.

FIG. 8 indicates results of measuring the chlorophyll a+b content and the β-carotene content in a leaf of the harvested Japanese mustard spinach. Numbers 1 and 3, which were subjected to foliar surface spraying with the aqueous solutions of yeast extract, had clearly increased chlorophyll a+b content and β-carotene content as compared to the control, or numbers 2 and 4 which were sprayed with the RNA isolate. There was a marked increase over the control even with the 100 mg/L aqueous solution of yeast extract of number 1. Therefore, when the purpose is to increase these pigments or nutrients in a plant body, this suggests that even a concentration of approximately 100 mg/L of the yeast extract in the foliar surface spray liquid is sufficient.

FIG. 9 indicates results of measuring the neoxanthin content and lutein content in a leaf of the harvested Japanese mustard spinach. Numbers 1 and 3, which were subjected to foliar surface spraying with the aqueous solutions of yeast extract, had increased neoxanthin content and lutein content as compared to the control, or numbers 2 and 4 which were sprayed with the RNA isolate. Moreover, when comparing numbers 1 and 3, number 3 had a clearly higher content. Therefore, this indicates that when the purpose is to increase the neoxanthin or lutein content in the plant body, the concentration of the yeast extract according to the present invention in the foliar surface spray liquid is preferably 300 mg/L rather than 100 mg/L.

In the taste evaluation, as a result of comparing the foliar surface spray of number 3 (using 300 mg/L of yeast extract) with the foliar surface spray of number 4 (using 90 mg/L of RNA), numerous comments indicated that the yeast extract test field of number 3 tasted sweet, had a favorable aftertaste, and tasted good, giving results indicating that the yeast extract according to the present invention also had an elevated effect of improving the taste of food.

Main comments in taste evaluation of Japanese mustard spinach (compared to control)

3: Aqueous solution of yeast extract: Sweet taste, favorable aftertaste, tastes good 4: Aqueous solution of RNA: Favorable flavor Given the results above, while an effect of promoting growth was, of course, observed with the yeast extract according to the present invention, other effects were also observed, such as promoting root lengthening, increasing amino acid content, increasing content of pigments and nutritive components, and improving quality of taste, and the yeast extract according to the present invention was confirmed to also contribute to improving added value. In addition, these results were higher even than those of RNA isolates. In view of the above, tests were next carried out to confirm whether similar effects could be achieved with other plants.

21 Embodiment 4> Comparison Test of Yeast Extract and RNA on Japanese Radish Leaf Japanese radish leaf (*Raphanus sativus* var. *longipinnatus*) is an annual plant of genus *Raphanus*, family Brassicaceae. Primarily the leaves and stem portions of this vegetable are consumed. Using commercially available "flower and vegetable soil" as the soil, Japanese radish leaf seeds were sown in planters (80 cm×30 cm). After sprouting, the Japanese radish leaf was permanently planted in a field and, after the true leaves appeared, the foliar surface spray liquid was misted onto the plants until the underside of the leaves was wet, at an interval of once in ten days. No temperature control was performed during cultivation, and the plants were harvested 90 days after permanent planting. The foliar surface spray liquid was as follows.

1: 100 mg/L aqueous solution of yeast extract obtained by Exemplary Manufacture 1.
2: 30 mg/L aqueous solution of RNA (manufactured by OMTEK). This is equivalent to the RNA concentration of the 100 mg/L aqueous solution of yeast extract in 1 above.
3: 300 mg/L aqueous solution of yeast extract obtained by Exemplary Manufacture 1.
4: 90 mg/L aqueous solution of RNA (manufactured by OMTEK). This is equivalent to the RNA concentration of the 300 mg/L aqueous solution of yeast extract in 3 above.
5: Water (control)

Evaluation was performed of an apparent size of a leaf portion and roots of the harvested Japanese radish leaf, an average weight of the leaves, free amino acid content of the leaves, and taste. For the taste evaluation, an experienced panel of six individuals was fed the edible portion without knowing which was the test field, and comments were obtained on differences in taste.

Results of Embodiment 4 are shown in FIGS. 10 to 13. FIG. 10 is a photograph of the entire harvested Japanese radish leaf. Numbers 1 to 4 indicate the respective type of foliar surface sprays noted above. FIG. 11 indicates the weight of the edible portion of the harvested Japanese radish leaf. Numbers 1 to 4 indicate the respective type of foliar surface sprays noted above.

As shown in FIGS. 10 and 11, even with the Japanese radish leaf, the yeast extract according to the present invention exhibited an effect of promoting growth similar to that with the Japanese mustard spinach, and had higher results as compared to RNA. However, when comparing numbers 1 and 3 (that is, the 100 mg/L aqueous solution of yeast extract and the 300 mg/L aqueous solution of yeast extract), number 1 had a significantly increased yield relative to the control, whereas the difference between number 3 and the control was, in fact, reduced. Therefore, this indicates that when the purpose is to increase the yield of Japanese radish leaf, the concentration of the yeast extract according to the present invention in the foliar surface spray liquid is preferably 100 mg/L rather than 300 mg/L.

FIG. 12 is a photograph of the root portion of the harvested Japanese radish leaf. Numbers 1 to 4 indicate the respective type of foliar surface sprays noted above. Even with the Japanese radish leaf, the yeast extract according to the present invention exhibited an effect of promoting root lengthening, with the 100 mg/L aqueous solution having a marked effect even higher than with the 300 mg/L aqueous solution.

FIG. 13 indicates results of measuring the free amino acid content in a leaf of the harvested Japanese radish leaf Numbers 1 to 4 indicate the respective type of foliar surface sprays noted above. In the results, the RNA test fields of numbers 2 and 4 exhibited almost no change from the control, but in the test fields of numbers 1 and 3 for the yeast extract according to the present invention, the threonine and proline content was higher than in the control, and particularly high results (1.3 times and 5.0 times, respectively) were obtained with the 300 mg/L aqueous solution of number 3.

In the taste evaluation, as a result of comparing each of the foliar surface spray of number 1 (using 100 mg/L of yeast extract) and the foliar surface spray of number 2 (using 30 mg/L of RNA) with the control, numerous comments indicated that the yeast extract test field of number 1 tasted sweet and had little astringency, giving results indicating that the yeast extract according to the present invention also had an elevated effect of improving the taste of food.

Main comments in taste evaluation of Japanese radish leaf (compared to control)

1: Aqueous solution of yeast extract: Sweet taste, little astringency

2: Aqueous solution of RNA: No different from control

As the above results make clear, by utilizing the yeast extract obtained by the present invention with cultivated plants, a superior effect of promoting growth, greater than with an RNA isolate, can be achieved with any plant, and early harvest or increased yield may be expected. In addition, an effect of promoting root lengthening becomes possible, and moreover various added values can be increased, such as increased content of threonine and proline in a harvested product, and improved taste.

The invention claimed is:

1. A foliar surface spray liquid comprising: a yeast extract having a peptide content of 5 wt % or more and an RNA content of 5 wt % or more, wherein the yeast extract in the foliar surface spray liquid is at a dry weight of between 1.0 ppm and 100,000 ppm.

2. The foliar surface spray liquid according to claim 1, wherein the yeast extract has a peptide content of 15 wt % or more, an RNA content of 25 wt % or more, and a free amino acid content of 4 wt % or less.

3. The foliar surface spray liquid according to claim 1, wherein the yeast extract is extracted from *Candida utilis* cells.

4. The foliar surface spray liquid according to claim 1, wherein the yeast extract is extracted from *Saccharomyces cerevisiae* cells.

5. The foliar surface spray liquid according to claim 1, further comprising a fertilizer.

6. The foliar surface spray liquid according to claim 5, wherein the fertilizer is a chemical fertilizer or an organic fertilizer.

7. The foliar surface spray liquid according to claim 6, wherein the chemical fertilizer is nitrogen, phosphorus, or potassium.

8. The foliar surface spray liquid according to claim 6, wherein the organic fertilizer is a plant oil cake, a fish meal, or a powdered marine algae.

9. A method of cultivating a plant, comprising:
spraying onto a leaf surface of a plant, or adding to soil or a hydroponic solution used in plant cultivation, a composition for plants containing a yeast extract having a peptide content of 5 wt % or more and an RNA content of 5 wt % or more.

10. The method of cultivating a plant according to claim 9, wherein the yeast extract in the foliar surface spray liquid according to claim 1 is at a concentration of 100 mg/L to 300 mg/L.

11. The method of cultivating a plant according to claim 9, wherein the plant is a tomato.

12. The method of cultivating a plant according to claim 9, wherein the plant is a Japanese mustard spinach.

13. The method of cultivating a plant according to claim 9, wherein the plant is a Japanese radish leaf.

14. The method of cultivating a plant according to claim 9, wherein the plant is a tomato, and wherein the yeast extract in the foliar surface spray liquid according to claim 1 is at a concentration of 300 mg/L.

15. The method of cultivating a plant according to claim 9, wherein the plant is a Japanese mustard spinach, and wherein the yeast extract in the foliar surface spray liquid according to claim 1 is at a concentration of 200 mg/L or more.

16. The method of cultivating a plant according to claim 9, wherein the plant is a Japanese radish leaf, and wherein the yeast extract in the foliar surface spray liquid according to claim 1 is at a concentration of 200 mg/L or less.

17. The method of cultivating a plant according to claim 9, wherein the plant is from the family Brassicaceae.

* * * * *